(12) United States Patent  (10) Patent No.: US 8,951,303 B2
Dehoff et al.  (45) Date of Patent: Feb. 10, 2015

(54) FREEFORM FLUIDICS

(75) Inventors: Ryan R. Dehoff, Knoxville, TN (US);
Randall F. Lind, Loudon, TN (US);
Lonnie L. Love, Knoxville, TN (US);
William H. Peter, Knoxville, TN (US);
Bradley S. Richardson, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 141 days.

(21) Appl. No.: 13/493,683

(22) Filed: Jun. 11, 2012

(65) Prior Publication Data

US 2013/0331949 A1  Dec. 12, 2013

(51) Int. Cl.
*A61F 2/54* (2006.01)
*A61F 2/74* (2006.01)
*B25J 15/10* (2006.01)
*A61F 5/10* (2006.01)
*B25J 9/14* (2006.01)
*A61F 2/58* (2006.01)
*A61F 2/68* (2006.01)
*A61F 5/01* (2006.01)

(52) U.S. Cl.
CPC ............ *B25J 9/144* (2013.01); *A61F 2002/741* (2013.01); *A61F 2/583* (2013.01); *A61F 2002/6836* (2013.01); *A61F 2005/0155* (2013.01); *A61F 5/013* (2013.01); *Y10S 901/37* (2013.01)
USPC ..................... 623/26; 623/64; 602/21; 901/37

(58) Field of Classification Search
CPC ... A61K 9/0097; A61F 2002/741; B25J 9/144
See application file for complete search history.

(56) References Cited

U.S. PATENT DOCUMENTS

| | | | |
|---|---|---|---|
| 4,521,150 A * | 6/1985 | Pigeon et al. | 414/749.4 |
| 5,113,117 A | 5/1992 | Brooks et al. | |
| 5,529,359 A * | 6/1996 | Borcea et al. | 294/207 |
| 6,844,518 B1 | 1/2005 | Coons et al. | |
| 7,718,105 B2 | 5/2010 | Tye et al. | |
| 7,887,729 B2 | 2/2011 | Tye et al. | |
| 8,469,424 B2 * | 6/2013 | Takenaka et al. | 294/198 |
| 2004/0106914 A1 * | 6/2004 | Coppeta et al. | 604/892.1 |
| 2006/0243086 A1 | 11/2006 | Cutkosky et al. | |

(Continued)

FOREIGN PATENT DOCUMENTS

| | | | | |
|---|---|---|---|---|
| DE | 197 55 465 A1 * | 6/1999 | | A61F 2/54 |
| WO | 2010099175 | 9/2010 | | |
| WO | WO 2011/033946 A1 * | 3/2011 | | F15B 11/16 |

OTHER PUBLICATIONS

DE 197 55 465 A1 (Jun. 17, 1999) computer generated English translation.*

(Continued)

*Primary Examiner* — David H Willse
(74) *Attorney, Agent, or Firm* — Novak Druce Connolly Bove + Quigg LLP

(57) ABSTRACT

A robotic, prosthetic or orthotic member includes a body formed of a solidified metallic powder. At least one working fluid cylinder is formed in the body. A piston is provided in the working fluid cylinder for pressurizing a fluid in the cylinder. At least one working fluid conduit receives the pressurized fluid from the cylinder. The body, working fluid cylinder and working fluid conduit have a unitary construction. A method of making a robotic member is also disclosed.

20 Claims, 7 Drawing Sheets

(56) References Cited

U.S. PATENT DOCUMENTS

| | | |
|---|---|---|
| 2008/0082301 A1 | 4/2008 | Haskell et al. |
| 2009/0108605 A1 | 4/2009 | Becker et al. |
| 2009/0177309 A1 | 7/2009 | Kozlak |
| 2010/0065142 A1 | 3/2010 | McMasters et al. |
| 2010/0218626 A1 | 9/2010 | Love et al. |
| 2011/0196509 A1 | 8/2011 | Jansen et al. |

OTHER PUBLICATIONS

Allanic et al. (1992). "Stereophotolithography: A Brand New Machinery," Solid Freeform Fabrication Symposium, pp. 260-271, Austin TX.

* cited by examiner

FREEFORM FLUIDICS

STATEMENT REGARDING FEDERALLY SPONSORED RESEARCH

This invention was made with government support under contract No. DE-AC05-00OR22725 awarded by the U.S. Department of Energy. The government has certain rights in this invention.

FIELD OF THE INVENTION

The present invention relates to additive manufacturing, and more specifically to additive manufacturing for prosthetics, robotics and orthotics.

BACKGROUND OF THE INVENTION

Emerging additive manufacturing processes are enabling a new perspective on the design of mechanical systems. Additive manufacturing, like nature, builds structures layer by layer rather than by removal of material. This approach to manufacturing enables the synthesis of components and systems that have previously been impossible. The first additive processing systems based on stereolithography (3D printing) were introduced in the late 1980's. Today, there are many different approaches, including Stereolithography (SLA), Selective Layer Sintering (SLS), Fused Deposition Modeling (FDM), Solid Ground Curing (SGC), and Laminated Object Manufacturing (LOM) among others, to construct a part layer by layer. The primary advantage of additive manufacturing is that complexity has little incremental cost. Unlike traditional machining practices which begins with a block of material and then removes material from that block to create a part, additive manufacturing decomposes the final part into layers and builds the part layer by layer. Parts can be made with voids (reducing weight and material usage) and additional complexity does not waste material or cost additional machining time.

The earliest additive manufacturing systems focused on polymers and plastics. Today, there are many emerging metal based additive manufacturing systems. Direct manufacturing technologies (E-Beam, Laser and Ultrasonic deposition) enables manufacturing using conventional metal alloys. These manufacturing technologies radically change the types of components that can be made. It is possible to build more anthropomorphic components or incorporate lattice structures for weight reduction or selective compliance where desired. Ultrasonic additive manufacturing uses a combination of additive and subtractive techniques enabling precise machining of intricate components and channels while simultaneously merging dissimilar materials. This low temperature process enables incorporation of sensitive materials such as sensors, wires, even fiber optics directly into the structure. However, whether metal or plastic, all applications of the systems have only focused on the development of mechanical components.

Examples in the literature of various additive manufacturing technologies can be found in A. Allanic, C. Medard and P. Schaeffer, "Stereophotolithography: A Brand New Machinery," Solid Freeform Fabrication Symposium, pp. 260-271, Austin Tx, 1992; Y. Hou, T. Zhao, C. Li and Y. Ding, "The Manufacturing of Rapid Tooling by Stereo Lithography," Adv. Materials Research Vols. 102-104, pp. 578-582, 2010; J. Song, Y. Li, Q. Deng and D. Hu, "Rapid Prototyping Manufacturing of Silica Sand Patterns Based on Selective Laser Sintering," Journal of Materials Processing Technology, Vol. 187-188, pp. 614-618, 2007; L. Aijun, Z. Zhuohui, W. Daoming and Y. Jinyong, "Optimization Method to Fabrication Orientation of Parts in Fused Deposition Modeling Rapid Prototyping," Int. Conf. on Mechanic Automation and Control Engineering (MACE), pp. 416-419, 2010; X. Zhang, B. Zhou, Y. Zeng and P. Gu, "Model Layout Optimization for Solid Ground Curing Rapid Prototyping Processes," Robotics and Computer-Integrated Manufacturing, Vol. 18, No. 1, pp. 41-51, 2002; H. Windsheimer, N. Travitzky, A. Hofenauer and P. Greil, "Laminated Object Manufacturing of Preceramic-Paper-Derived Composites," Advanced Materials, Vol. 19, No 24, pp. 4515-4519, 2007. The disclosures of these references are hereby incorporated by reference.

The basic mechanical design and fabrication of fluid powered systems has changed little since the start of the industrial revolution. Mechanical structure, actuators (motors), electronics and sensors are all fabricated with different processes and then integrated into the final system during the assembly process. As a result, systems tend to be larger, heavier, more complex and expensive than is necessary.

Mesofluidics is an approach to miniaturization of fluidic actuation and control that enables highly integrated, energy efficient hydraulic systems. Like the human form, the miniature hydraulic actuators, along with the fluid channels, blend into the structure enabling highly integrated systems. The power and stress levels of the hydraulic systems are approximately an order of magnitude greater than human muscles, enabling strength and packaging superior to nature. Today, mesofluidic devices are manufactured using conventional fabrication practices. Recent initiatives have focused on the development of low-cost titanium materials and manufacturing techniques with a target of $10/lb for the final manufactured part. Other efforts have focused on the development of low-cost titanium powders that, when combined with additive manufacturing processes, achieve this aggressive goal. Metal additive manufacturing systems, like nature, build parts in an additive, rather than subtractive process. The integration of the actuators and fluid conduits with the structure has the advantage of compactness, ease of assembly and maintenance with increased reliability.

In 2008, sales of components exceeded $14B and sales of fluid powered systems (agriculture, construction and manufacturing equipment) was well into the hundreds of billions of dollars. Furthermore, a recent study conducted by the Oak Ridge National Laboratory (ORNL), the National Fluid Power Association (NFPA) and 23 leading fluid power manufacturers and users quantified that a) fluid powered equipment consumes between 1.95 and 2.89 Quads/year and b) the average efficiency of fluid powered equipment is 21%. A 5% improvement in average efficiency could save US industry and consumers 0.4 Quad/year, nearly $10B/year. Unlike the automotive industry, the fluid power industry has had little innovation in the past 40 years.

SUMMARY OF THE INVENTION

A robotic, prosthetic or orthotic member includes a body formed of a solidified metallic powder. At least one working fluid cylinder is formed in the body. A piston is provided in the working fluid cylinder for pressurizing a fluid in the cylinder. At least one working fluid conduit receives the pressurized fluid from the cylinder. The body, working fluid cylinder and working fluid conduit have a unitary construction. The working fluid can be a liquid or a gas.

The robotic, prosthetic or orthotic member can have at least one master cylinder and at least one slave cylinder. The working fluid conduit conducts working fluid from the master cylinder to the at least one slave cylinder. The slave cylinder has a unitary construction with the body, the master cylinder, and the working fluid conduit. The working fluid conduit can be curved.

The body can have a unitary mesh. The unitary mesh can have at least two different edge lengths. The mesh edge lengths of the unitary mesh can be variable. The mesh edge lengths can change with changing position in three dimensions.

The robotic, prosthetic or orthotic member can include a piston rod for driving the piston, and a motor for driving the piston rod. A motor housing can be provided in the body for the motor. The motor housing can be unitary with the body, the piston cylinder and the working fluid conduit.

The motor can be connected to a cam. The cam drives the piston rod. The slave cylinders can have a piston and a drive rod connected to the piston. The drive rod can be connected to a drive element. The robotic member can include a second slave cylinder having a piston with a drive rod connected to the drive element. The slave cylinders and drive rods can be connected antagonistically to the drive element The robotic, prosthetic or orthotic member can also include an additional master cylinder. One of the master cylinders can be connected by a working fluid conduit to one of the slave cylinders for movement of the drive element in a first direction, and the other of the master cylinders can be connected by a working fluid conduit to the other of the slave cylinders for movement of the drive element in a second direction. The first direction can be opposite to the second direction, and movement of the drive element in the first direction with movement of the drive rod of the first slave cylinder can cause retraction of the drive rod of the other slave cylinder.

The robotic, prosthetic or orthotic member can have a plurality of drive elements. Each master cylinder can be connected to a plurality of slave cylinders. The slave cylinders correspond to and are connected to the drive elements, wherein operation of one master cylinder will cause operation of the corresponding slave cylinders and movement of the drive elements in a first direction, and operation of the other of the master cylinders will cause operation of the corresponding slave cylinders and movement of the drive elements in a second direction.

The drive elements can be the fingers of a robotic, prosthetic or orthotic hand. The robotic, prosthetic or orthotic member can include a motor and a motor housing in the body for the motor. The motor housing can be unitary with the body, the master cylinders, the slave cylinders, and the working fluid conduit. The motor can be connected to a cam, the cam operatively driving the pistons of the master cylinders.

A method of making a robotic, prosthetic or orthotic member includes the step of providing to a rapid prototyping machine an algorithm for the robotic member in the format of an STL file for example. The algorithm is capable of directing the machine to form from a metallic powder a body, at least one working fluid cylinder formed in the body, and at least one working fluid conduit for receiving a pressurized fluid from the working fluid cylinder. The body, working fluid cylinder and working fluid conduit have a unitary construction. The method can include the step of placing a piston in the working fluid cylinder. The working fluid can be a liquid or a gas.

BRIEF DESCRIPTION OF THE DRAWINGS

There are shown in the drawings embodiments that are presently preferred it being understood that the invention is not limited to the arrangements and instrumentalities shown, wherein.

DETAILED DESCRIPTION OF THE INVENTION

Figure 1:
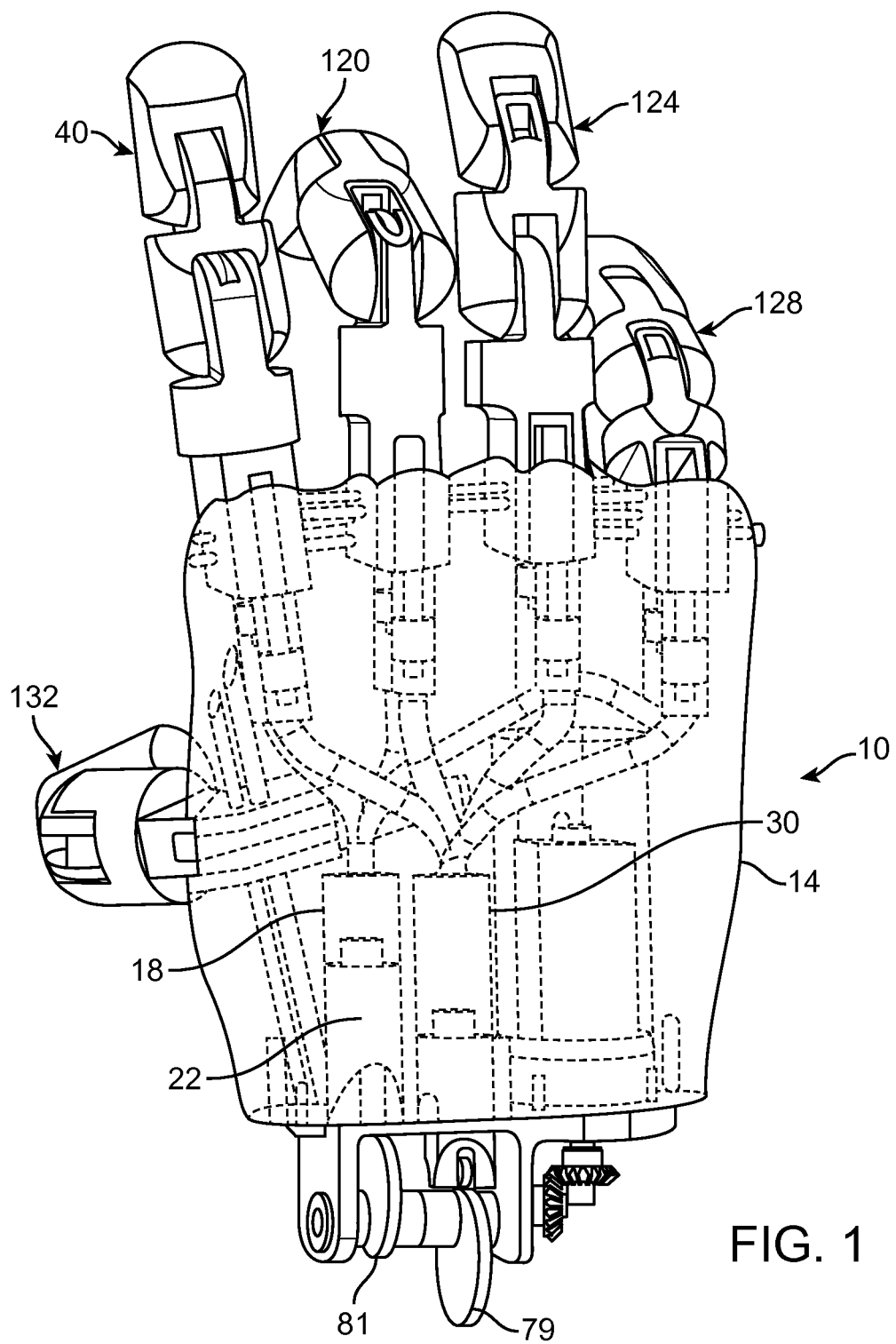
FIG. 1 is a perspective view, partially in phantom, of a prosthetic according to the invention.

There is shown in FIGS. 1-8 a robotic, prosthetic or orthotic member according to an embodiment of the invention. The robotic, prosthetic or orthotic member 10 includes a body 14 formed of a solidified metallic powder. At least one working fluid cylinder 18 is defined by the body. A piston 22 is provided in the working fluid cylinder 18 for pressurizing a fluid in the cylinder. At least one working fluid conduit 44 receives the pressurized fluid from the cylinder 18.

The body 14, working fluid cylinder 18 and working fluid conduit 44 have a unitary construction. The term "unitary construction" as used herein means that the body 14, working fluid cylinder 18 and working fluid conduit 44 is made as a single piece during manufacturing. Thus, a unitary component has a monolithic construction for the entire component, and is different from a component that has been made from a plurality of component pieces that have been joined together to form a single component.

Figure 3:
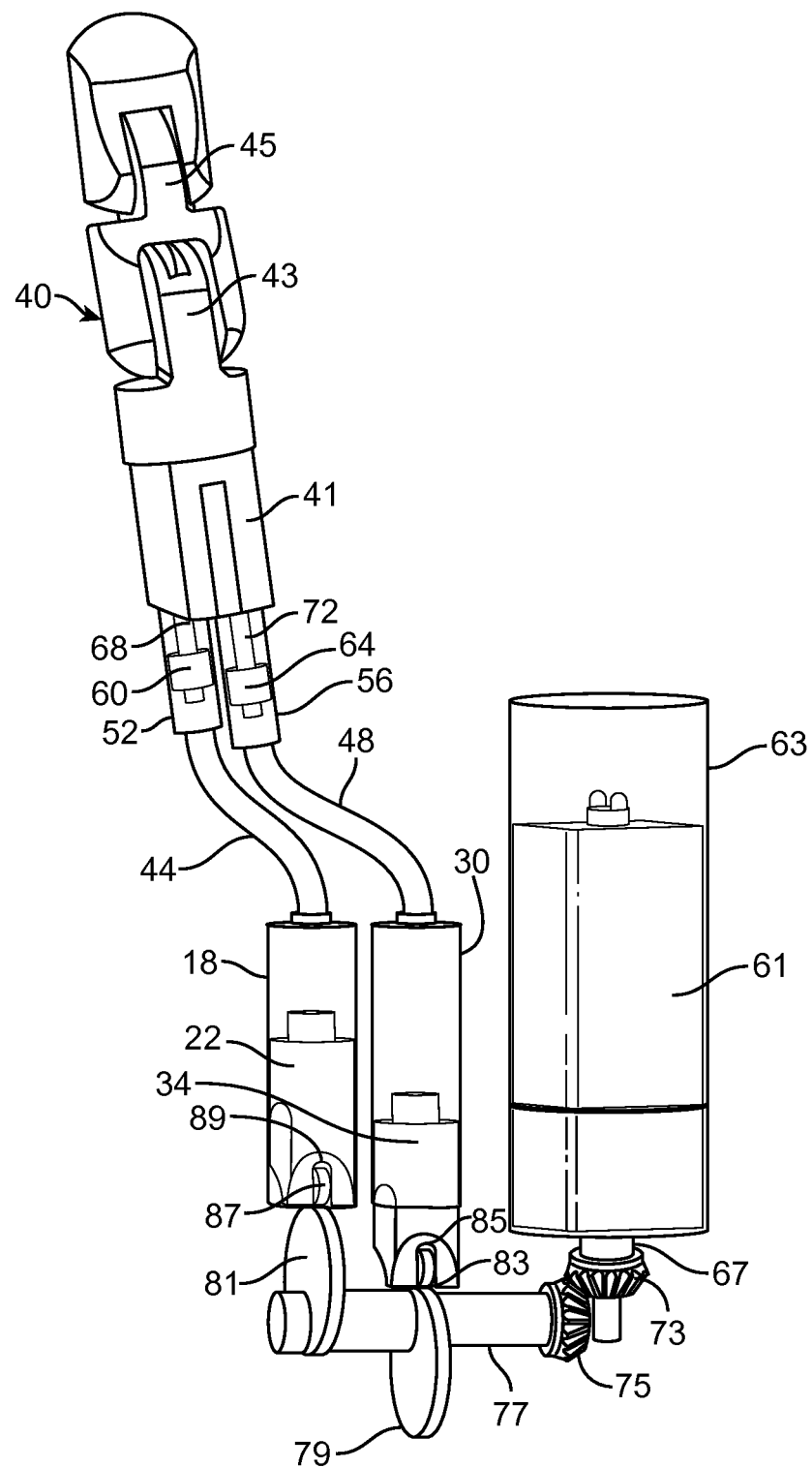
FIG. 3 is a negative perspective view of a master and slave piston assembly with the body removed for clarity.

The robotic, prosthetic or orthotic member 10 can have antagonistic, paired working fluid cylinders as shown in FIG. 3. The working fluid cylinder 18 can be paired with an antagonistic working fluid cylinder 30, having a piston 34. The term antagonist refers to the action of the cylinders 18, 30 to drive opposite movement of a robotic device. As one piston advances under an applied force to move the robotic device, the other or antagonistic piston is forced in the opposite direction by the same movement of the robotic, prosthetic or orthotic device. The working fluid will flow into and out of the cylinders from one or more working fluid conduits 44, 48.

In the example of FIG. 3, the robotic, prosthetic or orthotic device is a finger 40; however, the invention has utility in other robotic, prosthetics or orthotic applications such as arms, legs, feet and other uses where such antagonistic actuation is required to mimic extension and flexion movements. The robotic, prosthetic or orthotic device further can be selected from a variety of non-anthropomorphic devices such as claws, jaws or various other mechanical or sensory devices. The pistons 22 and 34 of the working cylinders 18, 30 can be directly connected to the robotic device by any suitable connection, such as drive or connecting rods and pivotal connections, pin and groove connections, and others.

Figure 2:
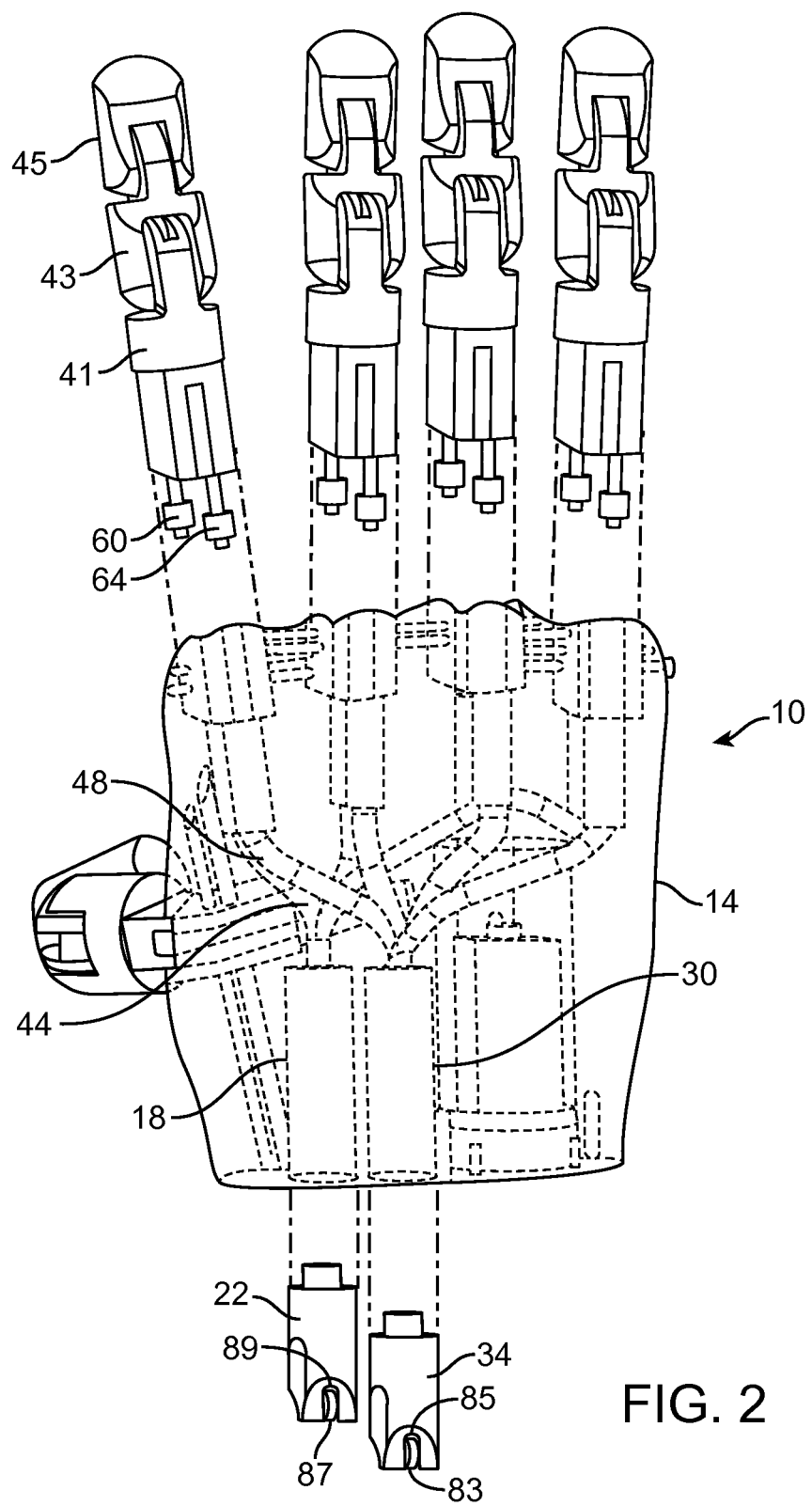
FIG. 2 is a partially exploded view.

In the embodiment shown the working cylinders 18, 30 are provided as master cylinders which act to drive one or more slave cylinders. In this way, mechanical action on the piston of a single master cylinder can be multiplied by the working fluid across many slave cylinders. This is particularly useful in a robotic, prosthetic or orthotic hand, where a single master cylinder piston can be operated to drive pistons in several slave cylinders which actuate prosthetic fingers as shown in FIGS. 1 and 2.

A master-slave cylinder system is shown in FIG. 3, where the working fluid cylinders 18 and 30 are provided as master cylinders and working fluid conduits 44, 48 communicate with slave cylinders 52, 56. The body 14 is not shown for clarity and that the master cylinders 18 and 30, working fluid conduits 44, 48 and slave cylinders 52, 56 are defined by the body 14. Pistons 60, 64 in the slave cylinders have drive or connecting rods 68, 72 which connect to the robotic device such as finger 40 by any suitable connecting structure. The working fluid conduits 44, 48 conduct working fluid from the master cylinders 18, to the slave cylinders 52, 56 such that piston motion imparted to the master pistons 22, 34 will be imparted to the slave pistons. The slave cylinders 52, 56 have a unitary construction with the body 14, the master cylinders 18 and 32, and the working fluid conduits 44, 48.

The additive manufacturing process permits the formation of the body 14, master cylinders 18 and 30, slave cylinders 52, 56, and working fluid conduits 44, 48 in an almost infinite variety of relative positions, sizes, and shapes. The working fluid conduits 44, 48 can be curved (non-linear), can be shaped so as to avoid other structures in the prosthetic, and can be of any length, cross section and diameter such dimensions can vary continuously if desired.

The pistons of the working fluid cylinders can be driven by suitable structure such as a motor 61. A motor housing 63 can be provided in the body 14 for the motor 61. The motor housing 63 can be unitary with the body 14, master cylinders 18 and 30, slave cylinders 52, 56, and working fluid conduits 44, 48. The motor 61 can be of any suitable design. The motor is preferably light weight and with a power rating suitable for the task, in the case of a prosthetic hand able to deliver to the fingers power resembling that of a human grip. In some examples there may be two or more motors that drive separate fluidic circuits to control different movements. For example, a separate motor may be used to control the extension or flexion of a particular finger or thumb, or some other individual movable component of a robotic, prosthetic or orthotic device.

The motor 61 can be connected to drive the pistons 22, 34 by suitable connecting structure. In the embodiment of FIG. 3, the motor 61 has a drive shaft 67 having a first gear 73. The first gear 73 meshes with a second gear 75 and to a cam shaft 77. The cam shaft 77 can have a first cam 79 and a second cam 81. The first cam 79 communicates with a cam follower 83 that is rotatably mounted in seat 85 of piston 34. The rotation of cam shaft 77 will rotate cam 79 which will contact cam follower 83 to drive the piston 34 forward in the working fluid cylinder 30. This will cause the working fluid to be forced through the working fluid conduit 48 and into the slave cylinder 56. The working fluid in the slave cylinder will drive the piston 64 forward which will cause the connecting rod 72 to advance and move the prosthetic drive element or robotic device such as finger 40. Similarly, the second cam 81 will contact cam follower 87 in seat 89 to drive the piston 22 forward and working fluid through the working fluid conduit 44 into slave cylinder 52. This will advance the piston 60 in the slave cylinder 52 and the associated connecting rod 60 to drive the prosthetic finger in a second and opposite direction. The cams 79 and 81 are out of phase such that as one piston, for example piston 22, is advancing the other piston 34 is retracting in the corresponding cylinder 30. This will permit working fluid to flow from the slave cylinder 56 back into the master cylinder 30 as the motion of the finger 40 under the action of the advancing piston 22 drives the antagonistically connected slave piston 64 in the opposite direction within the slave cylinder 56, which will cause working fluid to be exhausted through the working fluid conduit 48 and into the master cylinder 30.

Figure 7A:
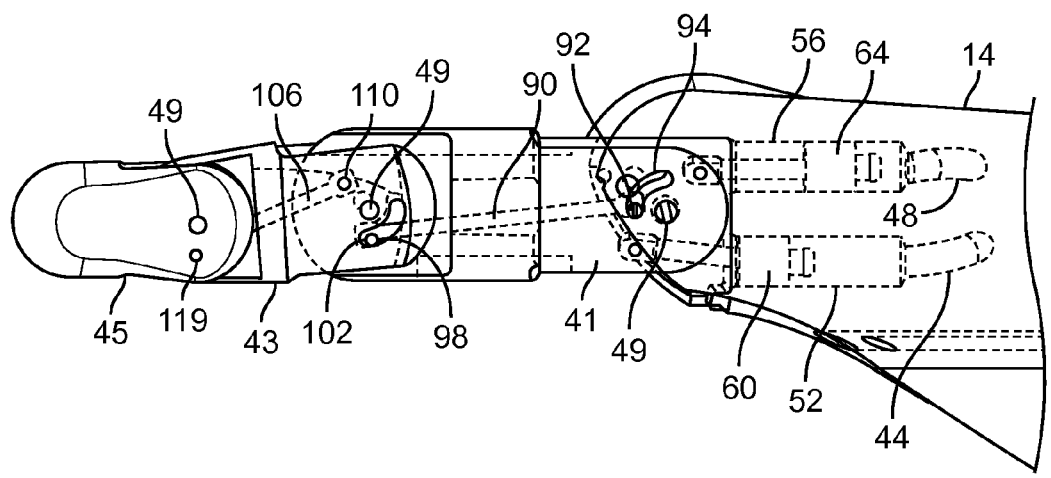
FIG. 7 A-B is a side elevation, partially in phantom, of a prosthetic finger in (A) extension and (B) flexion.
Figure 7B:
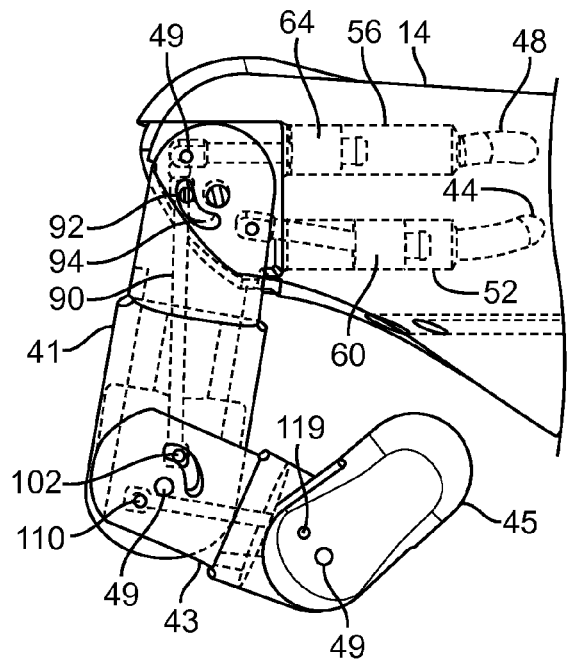

The invention has utility with a variety of different devices and prosthetics. The finger 40 shown in FIG. 3 can have differing designs. In the design shown the prosthetic finger 40 is segmented in two places to resemble a jointed human finger. The finger 40 has a proximal phalangeal section 41, an intermediate phalangeal section 43, and a distal phalangeal section 45. The proximal phalangeal section 41, intermediate phalangeal section 43, and distal phalangeal section 45 can be pivotally connected as shown in FIGS. 7A-B about pivot pins 49 or other suitable structure. A strut 90 can be pivotally connected at pin 92 within a curved slot 94, and at pin 102 within curved slot 98 to control the motion of the proximal phalangeal section 41 and intermediate phalangeal section 43. A strut 106 can be connected by pins 110 and 119 and can control movement between the intermediate phalangeal section 43 and the distal phalangeal section 45. The control struts 90 and 106 create relative movement of the proximal phalangeal section 41, intermediate phalangeal section 43, and a distal phalangeal section 45 between the extension position (FIG. 7A) and the flexion position (FIG. 7B).

The additive manufacturing process can be used to facilitate the incorporation into the robotic, prosthetic or orthotic device other structures such as valves by the unitary formation of valve seats, sensors by the unitary formation of placement and attachment sites in the prosthetic for the sensors, spring biasing by the unitary formation of the spring itself or by the unitary formation of the spring seats, conformal cooling conduits for circulating a coolant, embedded wires for inclusion of electronics and the like.

The drive elements can be the fingers of a robotic, prosthetic or orthotic hand. Many different drive elements are possible, and in the embodiment shown can be provided and arranged so as to mimic the human hand with, in addition to the index finger 40, the middle finger 120, ring finger 124, little finger 128 and thumb 132. Each finger can be operated by one or more antagonistic slave cylinders receiving working fluid from the master cylinders 18 and 30.

Any suitable additive manufacturing process and equipment can be utilized. Polymer based systems include fused deposition modeling and laser based fusion. Metal based systems include laser, electron beam and ultrasonics. Any suitable metallic powder material can be utilized. Suitable metallic powder starting materials include titanium (which has high strength, light weight, biocompatibility and corrosion resistance), cobalt-chrome (which is extremely hard), and aluminum.

The working fluid can be a liquid or a gas. The working fluid can be either a liquid in a hydraulic embodiment, liquid in a water embodiment or a gas in a pneumatic embodiment.

Figure 4:
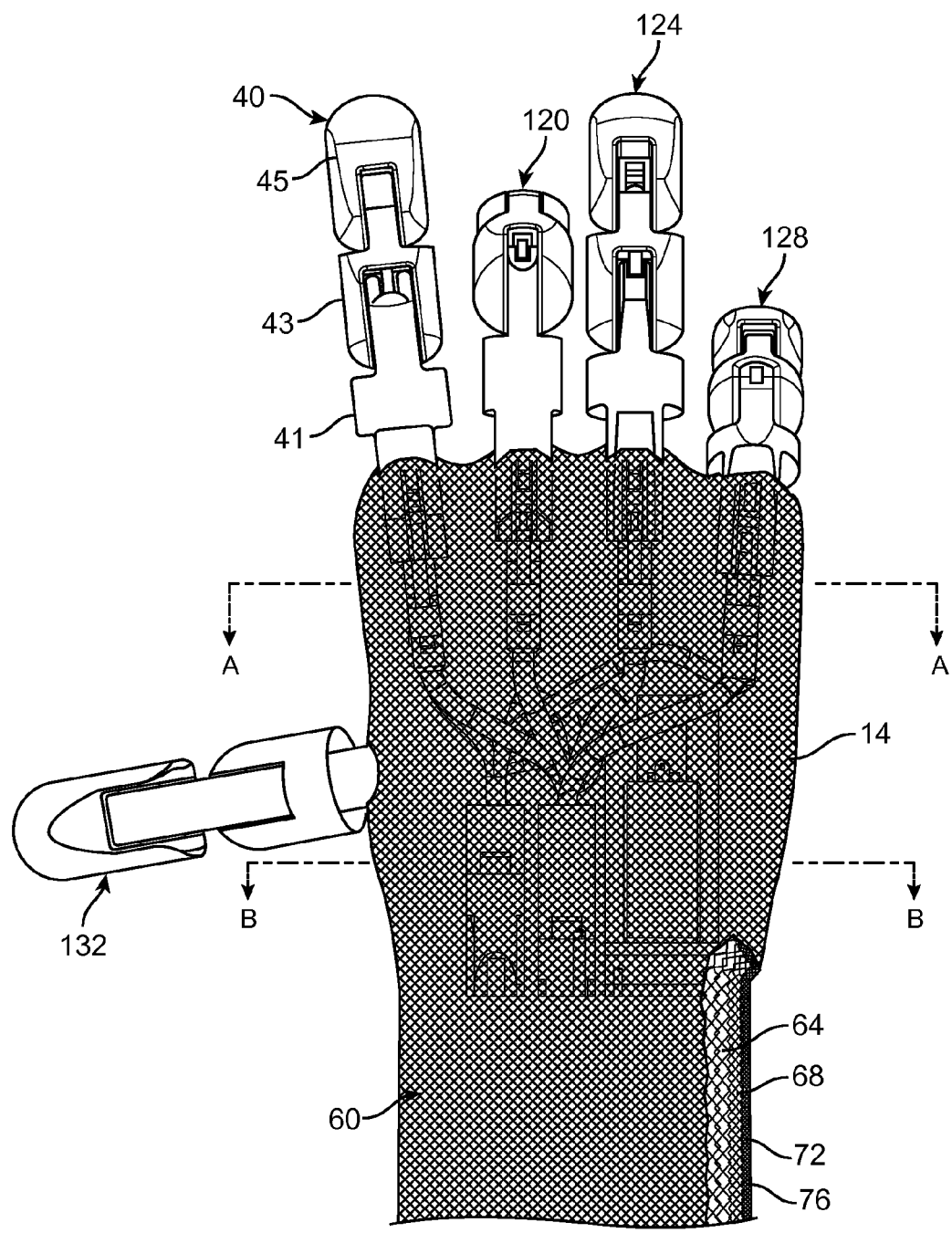
FIG. 4 is a plan view of a prosthetic hand assembly with mesh reinforcement, partially broken away to show internal features.

The body 14 can include a unitary structural lattice or mesh 60, as shown in FIG. 4. The mesh 60 can be of any suitable shape, but generally is an interconnected series of regularly spaced and interconnected side walls having a long dimension and defining between the side walls an elongated void. The interconnected side walls provide very significant structural strength, while the elongated voids provide light weight and lower cost as compared to a solid body. Such structures are known and can have differing geometries such as honeycomb, squares, rectangles, and parallelograms, among others. The additive manufacturing process is capable with appropriate programming of fashioning such structures around the other structures of the prosthetic (phantom lines in FIG. 4)

such as master cylinders 18 and 30, slave cylinders 52, 56, and working fluid conduits 44, 48, and to make the mesh 60 unitary with such structures.

Figure 5:
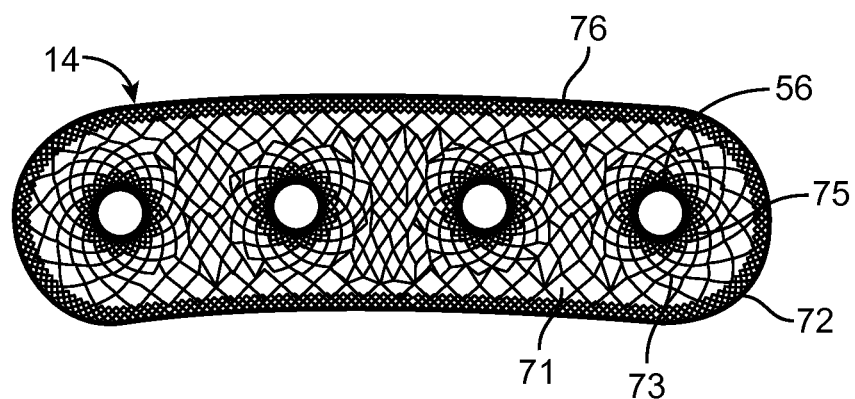
FIG. 5 is a cross section taken along line A-A in FIG. 4.
Figure 6:
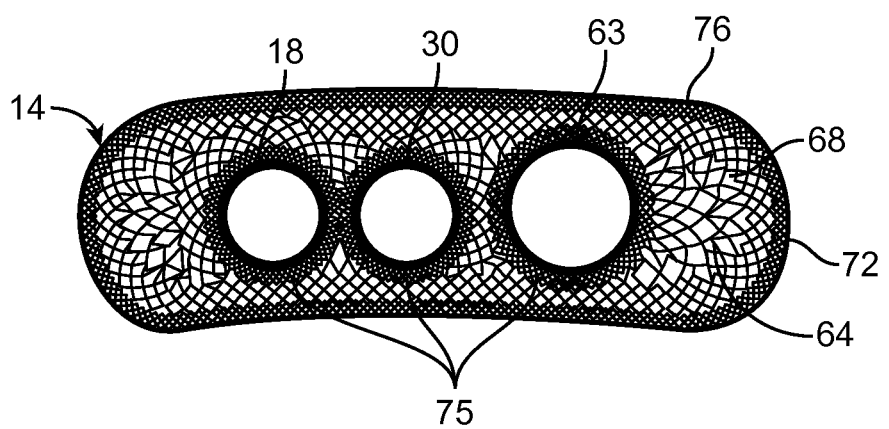
FIG. 6 is a cross section taken along line B-B in FIG. 4.

The mesh edge lengths can change with changing position in three dimensions. As shown in FIG. 4, the edge lengths of mesh 64 most interior to the prosthetic can be longer than the edge lengths of the mesh 68 closer to the surface. The edge lengths of the mesh region 72 closest to the surface can be still smaller for structural rigidity near the outer surface, and the outer surface can be fashioned as a solid layer 76 that is impervious to water and the elements. In this manner, the mesh closest to the surface of the prosthetic which could receive impacts and other damaging outside influences will have greater structural strength to resist these impacts, since smaller edge lengths in general will correspond to greater strength. The additive manufacturing process with suitable programming can transition to different edge lengths without seams or other regional borders that would provide locations for structural weakness. As shown in FIGS. 5-6, the edge lengths can be continuously variable from region to region within the prosthetic such as a greater edge length in a region 71 near the exterior surface 72 and smaller edge lengths progressing inwardly to a region of small edge lengths 73 and still smaller edge lengths 75 around the slave cylinder 56 (FIG. 5). As shown in FIG. 6, a region 75 of smaller edge lengths can be provided about the master cylinders 18 and 30 and motor housing 63. A region of greater edge length 64, progressing to regions of smaller edge lengths 68 and still smaller edge lengths 72 near the outer surface 76 which can be a layer of continuous material. The slave cylinder 56, master cylinders 18, 30 and fluid conduits 44, 48 are fashioned by the additive manufacturing process from a solid layer of material so as to be impervious to the working fluid. Any number of such variations of dimensional characteristics are possible depending on the design requirements of the particular component.

The additive manufacturing process can also be programmed to vary the thickness of the walls of the mesh from region to region. In this manner, the precise characteristics of the mesh including edge length, wall thickness and the metallic makeup of the wall material can be varied to impart structural characteristics where they are desired throughout the prosthetic. For example, in areas of the prosthetic that could be subject to temperature variation, the metallic powder that is used to form the mesh in these areas could be selected to better accommodate these temperature variations (eg, lower thermal expansion characteristics).

Figure 8A:
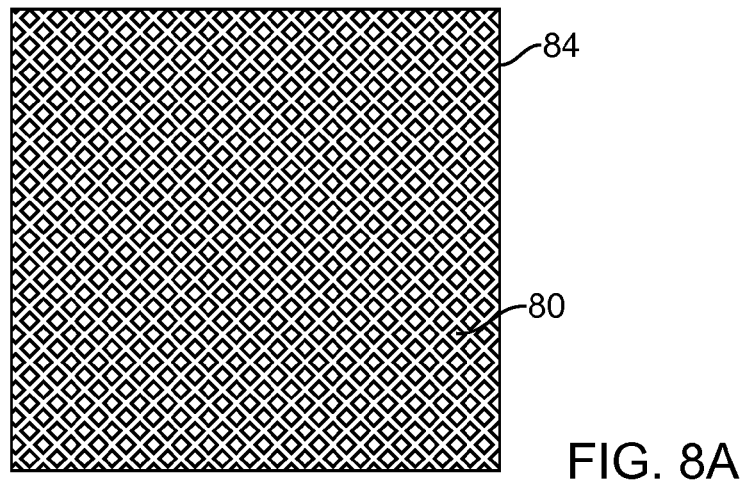
FIG. 8 A-C is a plan view of reinforcement mesh with (A) constant void spacing; (B) variable void spacing; and (C) graduated void spacing.
Figure 8B:
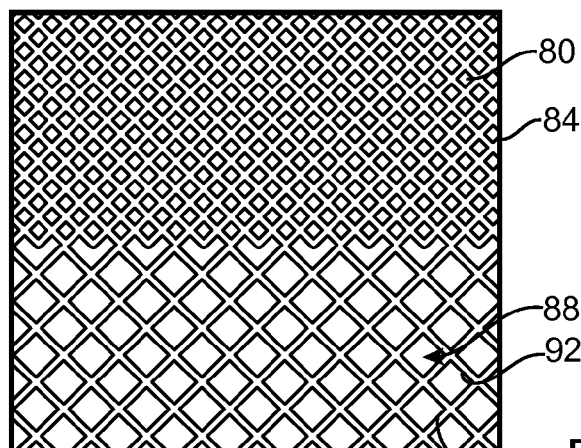
Figure 8C:
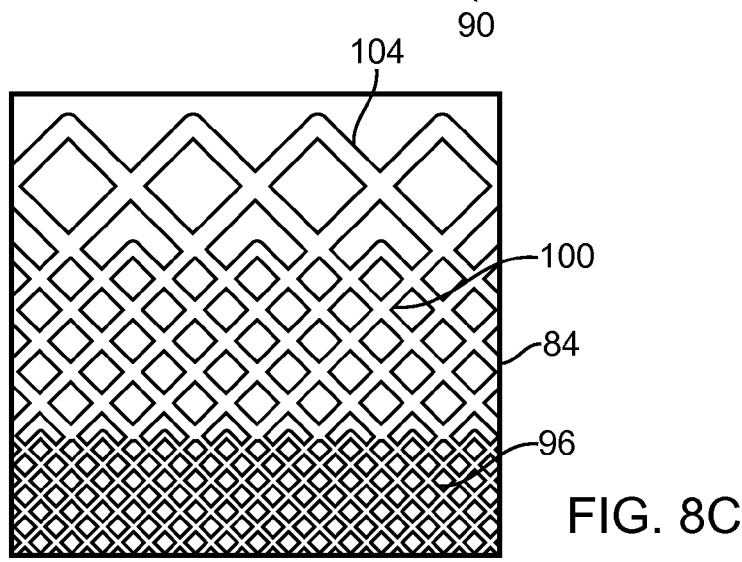

The unitary mesh can have at least two different edge lengths from region to region progressing in the lateral direction transverse to axial long dimension of the mesh cells. As shown in FIGS. 8A-C, the mesh 80 can in some places in the prosthetic have a single edge length (FIG. 8A). A solid border 84 can be provided as a surface treatment. In other areas of the prosthetic, the mesh 80 can transition to a mesh 88 having walls 90 with edges 92 of a greater dimension, which generally will provide lower weight (FIG. 8B). In yet another region of the mesh, the mesh can laterally transition from a mesh 96 with a first edge dimension, to a mesh 100 with a larger edge dimension, to a mesh 104 with still a larger edge dimension (FIG. 8C). The wall thickness can also vary from region to region, and can become greater from region 96 to region 100 and region 104 as shown, or the wall thickness can remain constant. The additive manufacturing process allows the mesh to transition laterally between regions in a relatively seamless fashion to avoid the creation of areas of structural weakness. The mesh edge length and wall thickness can be continuously varied in three dimensions wherever desired in the prosthetic.

A method of making a robotic, prosthetic or orthotic member includes the step of providing to a rapid prototyping machine an algorithm for the member in the format of an STL file for example. The algorithm is capable of directing the machine to form, from a metallic powder, a body, at least one working fluid cylinder formed in the body, and at least one working fluid conduit for receiving a pressurized fluid from the working fluid cylinder. The body, working fluid cylinder and working fluid conduit have a unitary construction. The method can include the step of placing a piston in the working fluid cylinder, as shown in FIG. 2, after which the fingers or other devices to be actuated by the pistons can be assembled.

The invention permits the manufacture of robotic, prosthetic or orthotic members that are complex but significantly lighter, using less material and at a reduced cost, than current techniques. As an example, a robotic or prosthetic arm (of similar size, shape and functionality as the human arm) can weigh under 5 lbs. Robotic arms that are currently available are larger, have fewer capabilities and have a very significant cost. The invention provides low-cost fluid powered systems that can follow nature's model of in-situ integration of sensing, power and structure during fabrication, enabling the development of new products not previously possible.

While the invention has been described in terms of specific embodiments, it is evident in view of the foregoing description that numerous alternatives, modifications and variations will be apparent to those skilled in the art. Accordingly, the invention is intended to encompass all such alternatives, modifications and variations which fall within the scope and spirit of the invention and the following claims.

We claim:

1. A robotic, prosthetic or orthotic member, comprising:
   a body formed of a solidified metallic or polymer powder or extrusion and further including a unitary, three dimensional mesh;
   at least one working fluid cylinder formed in the body;
   a piston in the working fluid cylinder for pressurizing a fluid in the cylinder;
   at least one working fluid conduit which receives the pressurized fluid from the cylinder; wherein the body, working fluid cylinder and working fluid conduit have a single unitary construction with each other.

2. The robotic, prosthetic or orthotic member of claim 1, wherein the cylinder is a master cylinder, and further comprising at least one slave cylinder, the working fluid conduit conducting working fluid from the master cylinder to the at least one slave cylinder, the slave cylinder having a unitary construction with the body, the master cylinder, and the working fluid conduit.

3. The robotic, prosthetic or orthotic member of claim 2, wherein the slave cylinders have a piston and a drive rod connected to the piston.

4. The robotic, prosthetic or orthotic member of claim 3, wherein the drive rod is connected to a drive element.

5. The robotic, prosthetic or orthotic member of claim 4, further comprising a second slave cylinder having a piston with a drive rod connected to the drive element, the slave cylinders and drive rods being connected antagonistically to the drive element.

6. The robotic, prosthetic or orthotic member of claim 5, further comprising an additional master cylinder, one of the master cylinders being connected by a working fluid conduit to one of the slave cylinders for movement of the drive element in a first direction, and the other of the master cylinders being connected by a working fluid conduit to the other of the slave cylinders for movement of the drive element in a second direction.

7. The robotic, prosthetic or orthotic member of claim 6, wherein the first direction is opposite to the second direction, and movement of the drive element in the first direction with movement of the drive rod of the first slave cylinder causes retraction of the drive rod of the other slave cylinder.

8. The robotic, prosthetic or orthotic member of claim 7, comprising a plurality of drive elements, each master cylinder being connected to a plurality of slave cylinders, the slave cylinders corresponding to and connected to the drive elements, wherein operation of one master cylinder will cause operation of the corresponding slave cylinders and movement of the drive elements in a first direction, and operation of the other of the master cylinders will cause operation of the corresponding slave cylinders and movement of the drive elements in a second direction.

9. The robotic, prosthetic or orthotic member of claim 8, wherein the drive elements are the fingers of a robotic, prosthetic or orthotic hand.

10. The robotic, prosthetic or orthotic member of claim 8, further comprising a motor and a motor housing in the body for the motor, the motor housing being unitary with the body, the master cylinders, the slave cylinders, and the working fluid conduit, the motor being connected to a cam, the cam operatively driving the pistons of the master cylinders, each master cylinder being in fluid connection with a plurality of slave cylinders so as to operate the plurality of slave cylinders with operation of the motor and the cam.

11. The robotic, prosthetic or orthotic member of claim 1, wherein the working fluid conduit is curved.

12. The robotic, prosthetic or orthotic member of claim 1, wherein the unitary mesh comprises at least two different edge lengths.

13. The robotic, prosthetic or orthotic member of claim 12, wherein the mesh edge lengths of the unitary mesh are variable.

14. The robotic, prosthetic or orthotic member of claim 13, wherein said mesh edge lengths change with changing position in three dimensions.

15. The robotic, prosthetic or orthotic member of claim 14, wherein the thickness of the mesh walls varies in three dimensions.

16. The robotic, prosthetic or orthotic member of claim 1, further comprising a piston rod for driving the piston, and a motor for driving the piston rod.

17. The robotic, prosthetic or orthotic member of claim 16, further comprising a motor housing in the body for the motor, the motor housing being unitary with the body, the piston cylinder and working fluid conduit.

18. The robotic, prosthetic or orthotic member of claim 16, wherein the motor is connected to a cam, the cam driving the piston rod.

19. The robotic, prosthetic or orthotic member of claim 1, wherein the working fluid is a liquid.

20. The robotic, prosthetic or orthotic member of claim 1, wherein the working fluid is a gas.

* * * * *